United States Patent
Stuermer et al.

(10) Patent No.: US 9,512,375 B2
(45) Date of Patent: Dec. 6, 2016

(54) METHOD AND APPARATUS FOR GENERATING A METHANE-CONTAINING SUBSTITUTE NATURAL GAS AND RELATED ENERGY SUPPLY SYSTEM

(71) Applicant: Zentrum fuer Sonnenenergie- und Wasserstoff-Forschung Baden-Wuerttemberg, Stuttgart (DE)

(72) Inventors: Bernd Stuermer, Stuttgart (DE); Michael Specht, Waldenbuch (DE); Volkmar Frick, Stuttgart (DE); Ulrich Zuberbuehler, Stuttgart (DE); Sebastian Thaler, Ludwigsburg (DE)

(73) Assignee: Zentrum fuer Sonnenenergie— und Wasserstoff-Forschung Baden-Wuerttemberg, Stuttgart (DE)

( * ) Notice: Subject to any disclaimer, the term of this patent is extended or adjusted under 35 U.S.C. 154(b) by 0 days.

(21) Appl. No.: 14/434,949

(22) PCT Filed: Oct. 9, 2013

(86) PCT No.: PCT/EP2013/071095
§ 371 (c)(1),
(2) Date: Apr. 10, 2015

(87) PCT Pub. No.: WO2014/057004
PCT Pub. Date: Apr. 17, 2014

(65) Prior Publication Data
US 2015/0284651 A1    Oct. 8, 2015

(30) Foreign Application Priority Data

Oct. 11, 2012   (DE) .................. 10 2012 218 526

(51) Int. Cl.
*C07C 27/00* (2006.01)
*C10L 3/08* (2006.01)
(Continued)

(52) U.S. Cl.
CPC .................. *C10L 3/08* (2013.01); *C07C 1/041* (2013.01); *C07C 1/044* (2013.01); *C07C 1/0435* (2013.01);
(Continued)

(58) Field of Classification Search
CPC ....... C10L 3/08; C10L 3/10; C10J 2300/1662; C10J 2300/0976; C10J 2300/0959; C10J 2300/1678; C10J 3/00
(Continued)

(56) References Cited

U.S. PATENT DOCUMENTS 3,967,936 A  *  7/1976  Tajbl ...................... C07C 1/048
                                                           48/197 R
4,849,571 A     7/1989  Gaffney
(Continued)

FOREIGN PATENT DOCUMENTS

DE  10 2011 014 971 A1  8/2012
EP       1 227 141 A2   7/2002
(Continued)

OTHER PUBLICATIONS

International Search Report (PCT/ISA/210) dated Mar. 5, 2014 with English translation (seven pages).
(Continued)

*Primary Examiner* — Jafar Parsa
(74) *Attorney, Agent, or Firm* — Crowell & Moring LLP

(57) ABSTRACT

The invention relates to a method and an apparatus for generating a methane-containing substitute natural gas from a carbon oxide-containing input gas and also to an energy supply system equipped with such an apparatus. According to the invention, the input gas is subjected to a methanation reaction where a superstoichiometric hydrogen fraction is established in the reactant gas. The product gas of the methanation reaction is divided by gas separation into a
(Continued)

Figure 1:
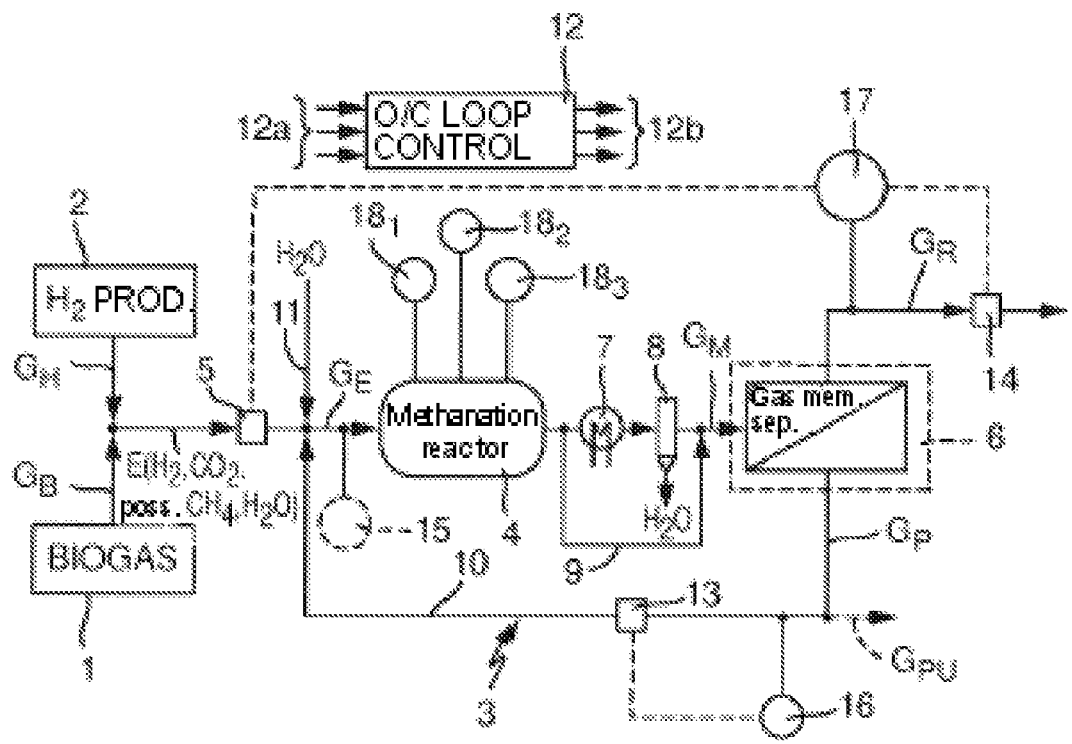

methane-containing retentate gas, which yields the substitute natural gas, and a hydrogen-containing permeate gas. At least some of the permeate gas is returned to the input gas and admixed therein to form the reactant gas for the methanation reaction. The invention may be used, for example, for renewable energy supply systems with biomass valorization.

6 Claims, 2 Drawing Sheets

(51) Int. Cl.
  C07C 1/04 (2006.01)
  C07C 1/12 (2006.01)
  C10J 3/82 (2006.01)
  C10L 3/10 (2006.01)
(52) U.S. Cl.
  CPC .............. C07C 1/0455 (2013.01); C07C 1/12 (2013.01); C10J 3/82 (2013.01); C10L 3/101 (2013.01); C10L 3/104 (2013.01); C07C 2523/38 (2013.01); C07C 2523/70 (2013.01); C10J 2200/09 (2013.01); C10J 2300/1662 (2013.01); C10L 2200/0492 (2013.01); C10L 2290/04 (2013.01); C10L 2290/42 (2013.01); C10L 2290/548 (2013.01); Y02E 50/10 (2013.01); Y02E 50/30 (2013.01); Y02P 20/133 (2015.11)
(58) Field of Classification Search
  USPC .................................................. 518/700, 702
  See application file for complete search history.

(56) References Cited

U.S. PATENT DOCUMENTS

| | | |
|---|---|---|
| 2002/0103407 A1 | 8/2002 | Hatanaka |
| 2010/0205863 A1 | 8/2010 | Biollaz et al. |
| 2010/0286292 A1* | 11/2010 | Wix .......................... C10L 3/08 518/702 |
| 2012/0091730 A1 | 4/2012 | Stuermer et al. |
| 2012/0208902 A1 | 8/2012 | Kresnyak et al. |

FOREIGN PATENT DOCUMENTS

| | | |
|---|---|---|
| WO | WO 2009/007061 A1 | 1/2009 |
| WO | WO 2010/115983 A1 | 10/2010 |

OTHER PUBLICATIONS

Gassner et al. "Integrated design of a gas separation system for the upgrade of crude SNG with membranes" Chemical Engineering and Processing: Process Intensification, 2009, pp. 1391-1404, vol. 48, Elsevier.

Gassner et al. "Combined mass and energy integration in process design at the example of membrane-based gas separation systems" Computers and Chemical Engineering, 2010, 10 pages, Elsevier.

Heyne et al. "Integration study for alternative methanation technologies for the production of synthetic natural gas from gasified biomass" 13th Conference on Process Integration, Modelling and Optimisation for Energy Saving and Pollution Reduction, Aug. 1, 2010, six pages, Department of Energy and Environment et al., Goeteborg, Sweden, XP055103849.

Kopyscinski et al. "Production of synthetic natural gas (SNG) from coal and dry biomass—A technology review from 1950-2009" Fuel, Feb. 6, 2010, pp. 1763-1783, vol. 89, No. 8, General Energy Research Department, Paul Scherrer Institut, CH-5232, Villigen PSI, Switzerland, XP055000387.

Sehested et al. "Methanation of CO over Nickel: Mechanism and Kinetics at High $H_2$/CO Ratios" The Journal of Physical Chemistry B, Feb. 1, 2005, pp. 2432-2438, vol. 109, No. 6, Haldor Topsoe et al, Lyngby, Denmark, XP 055103675.

Gassner et al. "Thermo-economic optimization of the integration of electrolysis in synthetic natural gas production from wood" Science Direct, 2008, pp. 189-198, Energy 33, Elsevier, Laboratoire d'Energetique Industrielle, Lausanne, Switzerland.

Gassner et al. "Methodology for the optimal thermo-economic, multi-objective design of thermochemical fuel production from biomass" Computers and Chemical Engineering, 2009, pp. 769-781, vol. 33, Laboratory for Industrial Energy Systems, Lausanne, Switzerland.

* cited by examiner

METHOD AND APPARATUS FOR GENERATING A METHANE-CONTAINING SUBSTITUTE NATURAL GAS AND RELATED ENERGY SUPPLY SYSTEM

The invention relates to a method and an apparatus for generating a methane-containing substitute natural gas from a carbon oxide-containing input gas and also to an energy supply system equipped with such a device.

Substitute natural gas (SNG) refers to gases which can be used in addition to or instead of natural gas and for this can be more particularly fed into existing gas or natural gas supply grids. For such feeding, the gases have to meet certain requirements, which are defined/standardized in relevant rules and regulations. For instance, the technical rules of the DVGW (Deutsche Vereinigung des Gas-und Wasserfaches e.V.) define in Code of Practice G 260 "Gas constitution" and Code of Practice G 262 "Utilization of gases from renewable sources in the public gas supply" the requirements to be met by combustible gases utilized for public gas supply. Essentially four types of gases are distinguished in that context. Base gases are the gases customarily distributed in a supply area. Conditioning gases are gases or gas mixtures which are admixed to the base gas, or to the gas to be fed, in order to establish certain combustion performance indicators. Supplementary gases are gases/gas mixtures which, in terms of composition and combustion performance indicators, differ significantly from the base gas and can be added to the base gas in a limited amount. Replacement gases are gases/gas mixtures which, notwithstanding a composition and/or indicators different than the base gas, have the same type of burning behavior as the base gas at the same gas pressure and equipment setting and therefore can be used instead of the base gas. Replacement gas is advantageous over supplementary gas by virtue of the greater flexibility it affords with regard to feedable volumes, but the gas to be fed then has to meet stricter quality requirements. One of the most important combustion performance indicators for natural gas and substitute natural gas is the so-called Wobbe index ($kWh/m^3_{std}$) which for example is between about 10.5 and 13.0 for natural gas of comparatively lower quality (L-gas group) and between about 12.8 and 15.7 for gas of comparatively higher quality (H-gas group).

Biomass has recently become more and more important as a source for substitute natural gas because biomass can be converted to yield a methane-rich gas which is usable as a substitute natural gas. Biomass is typically converted either by a thermochemical gasification reaction, which delivers a so-called synthesis gas, which contains hydrogen ($H_2$), carbon monoxide (CO) and carbon dioxide ($CO_2$) as principal constituents and is convertible by methanation into $CH_4$, or by biogas plants, which deliver a product gas consisting essentially of $CO_2$ and methane ($CH_4$).

It has already been variously proposed that renewably generated electric energy, generated for example in the form of solar and wind energy with a marked fluctuation over time, be used in the generation of substitute natural gas in order that said electric energy may be stored in this way as chemical energy. To this end, the electric energy generated is used to operate a hydrogen generating device, for example a water electrolysis plant, and the hydrogen generated by same is subjected together with a $CO_2$-containing gas, for example from a biomass conversion, to a methanation reaction yielding a product gas from which methane-containing substitute natural gas is obtainable. Laid-open publication WO 2010/115983 A1 of the applicant discloses an energy supply system whereby in this way a supplementary or replacement gas is provided and utilized in a variably specifiable supplementary/replacement gas quality suitable for feeding into a gas supply grid.

The article M. Gassner et al., Integrated design of a gas separation system for the upgrade of crude SNG with membranes, Chemical Engineering and Processing 48 (2009), pages 1391 to 1404, discloses a method and an apparatus for producing a methane-containing substitute natural gas from a methane synthesis of a gas obtained by thermochemical gasification of biomass, with hydrogen obtained by an electrolysis. The product gas from the methane synthesis is processed in a single-stage or multi-stage gas separation, in particular to remove the $CO_2$ present in the methanation reaction product gas there, to form the substitute natural gas. The permeate gas from the gas separation is sent into a combustion process. Similarly, the article M. Gassner and F. Maréchal, Combined mass and energy integration in process design at the example of membrane-based gas separation systems, Computers and Chemical Engineering, 2010, proposes a methane synthesis of a gas obtained by thermochemical gasification of biomass, with subsequent single- or multi-stage gas separation in order to provide from the gas separation a methane-rich substitute natural gas by the retentate gas, while the methane synthesis in this case is carried out without externally supplied hydrogen, and hydrogen-containing permeate gas from the gas separation is optionally recycled to the inlet side of the methane synthesis and sent into the product gas from the thermochemical gasification of biomass. For the composition of the product gas from the thermochemical gasification of biomass, which is used as input gas for the methanation reaction, amounts of 27% to 42% of $H_2$, 18% to 38% of $CO_2$, 15% to 28% of CO and 9% to 12% of $CH_4$ (all particulars in volume percent) are reported. This means that, in the input gas reacted there, the hydrogen fraction is in a highly substoichiometric range relative to the level of carbon oxides, i.e., CO and $CO_2$.

The methanation reaction is frequently performed as "chemical" methanation and catalytically augmented to this end, for which various catalytic materials are commonly used, such as nickel (Ni), ruthenium (Ru), iron (Fe), cobalt (Co), rhodium (Rh), palladium (Pd), platinum (Pt) and iridium (Ir). The methanation catalysts are subject to various deactivation mechanisms, in particular thermal sintering, carbon deposition, oxidation and poisoning by sulfur compounds, i.e., sulfide formation. To avoid thermal sintering, care must be taken to ensure that a certain maximum catalyst temperature is not exceeded in operation. Carbon deposition results inter alia from the Boudouard reaction and leads inter alia to fouling of the catalyst surface, to the blocking of pores and voids in the catalyst and to the physical destruction of the catalyst carrier material, for which it is customary to use a metal oxide, for example aluminum oxide, argillaceous earth or limestone.

Alternatively, the methanation reaction can be carried out as "biological" methanation, which involves a bacterial conversion of $CO_2$ with $H_2$ in an appropriate biochemical reactor at temperatures of typically less than 70° C.

It is an object of the present invention to provide a method and an apparatus of the type mentioned at the outset and also a corresponding energy supply system which each make it possible, in an improved manner in relation to the prior art reviewed above, for a methane-containing substitute natural gas to be obtained from a carbon oxide-containing input gas and utilized, for example by input of renewably generated electric energy and/or of biomass.

The invention achieves this object by providing a method for generating a methane-containing substitute natural gas from a carbon oxide-containing input gas, said method comprising subjecting the input gas to a methanation reaction and dividing a product gas obtained therefrom by gas separation into a methane-containing retentate gas, which yields the substitute natural gas, and a hydrogen-containing permeate gas, and returning at least some of the permeate gas to the input gas and admixing therein to form a corresponding reactant gas for the methanation reaction, wherein a superstoichiometric hydrogen fraction is established in the reactant gas for the methanation reaction.

The invention further achieves this object by providing an apparatus for producing a methane-containing substitute natural gas from a carbon oxide-containing input gas, said apparatus comprising a methanation reactor to obtain a product gas from a supplied reactant gas, a gas separation device for dividing the product gas into a methane-containing retentate gas, which yields the substitute natural gas, and a hydrogen-containing permeate gas, a permeate gas recycle to the inlet side of the methanation reactor and to the admixture there of the permeate gas to the input gas to form the reactant gas, and an open or closed loop control device for establishing a superstoichiometric hydrogen fraction in the reactant gas for the methanation reaction under open or closed loop control.

The invention moreover achieves this object by providing an energy supply system comprising a hydrogen generating device for generating hydrogen, a biomass conversion plant or some other CO2/CO source delivering a carbon oxide-containing gas, and an apparatus for producing a methane-containing substitute natural gas from a carbon oxide-containing input gas, said apparatus comprising a methanation reactor to obtain a product gas from a supplied reactant gas, a gas separation device for dividing the product gas into a methane-containing retentate gas, which yields the substitute natural gas, and a hydrogen-containing permeate gas, a permeate gas recycle to the inlet side of the methanation reactor and to the admixture there of the permeate gas to the input gas to form the reactant gas, and an open or closed loop control device for establishing a superstoichiometric hydrogen fraction in the reactant gas for the methanation reaction under open or closed loop control, wherein a device for supplying the hydrogen generated by the hydrogen generating device and the carbon oxide-containing gas as input gas is assigned to the apparatus.

In the method of the present invention, the input gas is subjected to a chemical or biological methanation reaction and the product gas obtained therefrom is divided by gas separation into a methane-containing retentate gas, which yields the substitute natural gas, and a hydrogen-containing permeate gas. At least some of the permeate gas is returned to the input gas and admixed therein to form a corresponding reactant gas for the methanation reaction. Characteristically, a superstoichiometric hydrogen fraction is established in the reactant gas for the methanation reaction.

It transpires that establishing a super-stoichiometric hydrogen fraction in the reactant gas for the methanation reaction has significant advantages over the conventional way of running a methanation, using a substoichiometric or at most just stoichiometric hydrogen fraction, specifically regarding a high degree of conversion for the carbon oxides, in particular $CO_2$ and $CO$, which are present in the input gas, and regarding reduced deactivation effects for any catalyst material typically present in the methanation reactor. To wit, the comparatively high hydrogen fraction in the reactant gas ensures virtually complete conversion of the carbon oxides into methane and a cooling effect is caused in the methanation reactor to avoid/ameliorate the temperature spikes known as hot spots. A further achievement is an inherently safe operation of the methanation with regard to the various catalyst deactivation effects, such as reduction in and/or avoidance of carbon depositions and also of sulfide formation, oxidation processes and thermal sintering of the catalyst material.

Gas separation separates hydrogen unconverted by the methanation as part of the permeate gas from the retentate gas. The retentate gas, which contains the generated methane as principal constituent, yields the desired substitute natural gas directly or after further gas processing. As required, the substitute natural gas thus obtained is providable in supplementary gas quality or replacement gas quality, for example for feeding into a public gas supply grid. Recycling the permeate gas makes it possible for the unconverted hydrogen present therein to be resupplied to the methanation reaction.

The methanation of $CO$ and $CO_2$ with $H_2$ to form methane ($CH_4$) and water ($H_2O$) proceeds primarily according to the following methanation reactions:

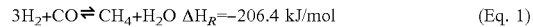

$$3H_2 + CO \rightleftharpoons CH_4 + H_2O \quad \Delta H_R = -206.4 \text{ kJ/mol} \quad \text{(Eq. 1)}$$

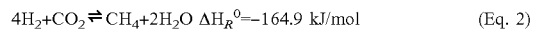

$$4H_2 + CO_2 \rightleftharpoons CH_4 + 2H_2O \quad \Delta H_R^0 = -164.9 \text{ kJ/mol} \quad \text{(Eq. 2)}$$

The two methanation reactions are linked together by the shift reaction

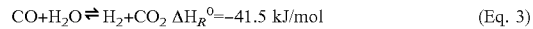

$$CO + H_2O \rightleftharpoons H_2 + CO_2 \quad \Delta H_R^0 = -41.5 \text{ kJ/mol} \quad \text{(Eq. 3)}$$

Owing to the strongly exothermic and volume-reducing hydrogenation of $CO$ and $CO_2$, the reactions work best at low temperatures, for example between 180° C. and 350° C., and high pressures. The large magnitude for the reaction enthalpy ($\Delta H_R^0$) of $CO$ methanation is indicative of nearly complete conversion at moderate temperatures, so the reverse reaction may in effect be neglected. $CO_2$ methanation proceeds predominantly in two steps, the $CO$ retroshift and the subsequent $CO$ hydrogenation, possibly also by direct methanation.

Because the hydrogen fraction in the reactant gas is superstoichiometric in this invention, the above reactions are each shifted in the direction of the hydrogen-free side, i.e., toward the right-hand side in the case of the two methanation reactions, and hence in the direction of increased conversion of carbon oxide. At the same time, the comparatively high hydrogen fraction in the reactant gas causes a shift in the subsequent, catalyst-relevant reaction equations such that the effects such as carbon formation and metal sulfide formation which are primarily responsible for catalyst deactivation are reduced:

$$C + 2H \rightarrow CH_4 \quad \text{(Eq. 4)}$$

$$C + CO_2 \rightarrow 2CO \quad \text{(Eq. 5)}$$

$$C + H_2O \rightarrow CO + H_2 \quad \text{(Eq. 6)}$$

$$NiS + H_2 \rightarrow Ni + H_2S \quad \text{(Eq. 7)}$$

$$Ni_3S_2 + 2H_2 \rightarrow 3Ni + 2H_2S \quad \text{(Eq. 8)}$$

$$NiO + H_2 \rightarrow Ni + H_2O \quad \text{(Eq. 9)}$$

The reactions as per the above equations 5 and 6 are followed by the reaction as per the above equation 1. A nickel catalyst was contemplated in the above equations 7 to 9 as representative of other conventional catalyst materials which can be used.

In one development of the invention, the stoichiometry factor of the reactant gas, which is defined as the ratio of the difference in the proportions of hydrogen and of carbon dioxide to the sum total of the carbon monoxide and carbon dioxide proportions, is maintained in the range above three and not more than fifteen. Defined in this way, the stoichiometry factor has a value of 3 when the hydrogen quantity is stoichiometric, a value of 7 when the hydrogen quantity is twice the stoichiometric quantity and a value of 11 when the hydrogen quantity is three times the stoichiometric quantity, all based on $CO_2$ conversion and $CO_2$ amount.

A development of the method according to the invention comprehends various possible advantageous alternatives for establishing the superstoichiometric hydrogen fraction for the methanation reaction. To this end, one or more selected process parameters are measured and used to adjust one or more process parameters in a suitable manner according to the measurements obtained. The quantities measured may be in particular the pressure, temperature and volume flow/amount of the gases involved and the determination of a pressure and/or temperature profile in the methanation reactor. The process parameters adjusted according to the measurements obtained may be in particular the amount of supplied input gas and/or permeate gas, the hydrogen fraction in the input gas, the pressure in the methanation reactor and/or the differential pressure chosen for gas separation.

In one of these alternatives, for instance, the hydrogen-containing permeate gas admixture to the input gas is advantageously closed-loop controllable to achieving a specified $CO_2/CO$ minimum conversion according to a specified $CO_2/CO$ gas volume flow of the input gas and a specified pressure difference between retentate gas and permeate gas. Recycling a sufficient amount of the hydrogen-containing permeate gas ensures the maintenance of a superstoichiometric hydrogen fraction in the reactant gas.

A further alternative embodiment of the invention is suitable for applications where the input gas used is a mixture of a hydrogen gas and of a gas which is rich in carbon oxide, i.e., $CO_2$ and/or $CO$. This is the case, for example, in systems where the $CO_2/CO$-rich gas comes from biomass conversion and is admixed, in a water electrolysis plant, with hydrogen generated using renewable electric power. In such applications, the hydrogen gas is meterable into the $CO_2/CO$-rich gas according to the amount and/or composition of the $CO_2/CO$-rich gas and depending on the amount and/or composition of the recycled permeate gas.

In one development of the invention, the methanation reactor is monitored for any catalyst deactivation and/or any hot spot displacement and once catalyst deactivation/hot spot displacement has been detected, the gas pressure in the methanation reactor and/or a water vapor fraction in the reactant gas is increased and/or the reactor temperature is adjusted, i.e., increased or decreased depending on the system and particular application. In one of these alternative embodiments, the pressure and/or temperature in the methanation reactor are measured at two or more successive measuring points in the gas flow direction and the corresponding pressure/temperature profile is used to detect the occurrence of hot spot displacement, which may be due in particular to an increasing deactivation of the catalyst. This effect can then be counteracted in a suitable manner by the measures referred to.

An apparatus according to the invention for producing a methane-containing substitute natural gas from a carbon oxide-containing input gas in the manner of the present invention comprises not only a methanation reactor and a downstream gas separation means but also a permeate gas recycle to the inlet side of the methanation reactor and an open or closed loop control device for establishing a superstoichiometric hydrogen fraction in the reactant gas for the methanation reaction under open or closed loop control. Such an open or closed loop control device ensures maintenance of the desired superstoichiometric hydrogen fraction in the reactant gas. More particularly, the apparatus according to the invention has the requisite means for conducting the method of the present invention.

In one embodiment of the invention, the apparatus for this also includes suitable sensor means to provide measured data for the open or closed loop control device. Depending on the measured data supplied, the open or closed loop control device engages via appropriate actuators into the process such that the hydrogen fraction in the reactant gas remains at a desired superstoichiometric value.

An energy supply system according to the present invention is equipped with an apparatus according to the invention for producing a methane-containing substitute natural gas. It further comprises a hydrogen generating device for generating hydrogen and a biomass conversion plant or some other $CO_2/CO$ source supplying a carbon oxide-containing gas. They supply the input gas for the methanation as a mixture of carbon oxide-containing gas and hydrogen gas. The hydrogen generating device may be operated, for example, in the form of a water electrolysis plant using renewably generated electric energy. This then constitutes a system whereby renewably generated electric energy and carbon oxides recovered from biomass or otherwise provided can be used in an advantageous manner with a high degree of efficiency for producing substitute natural gas.

Figure 2:
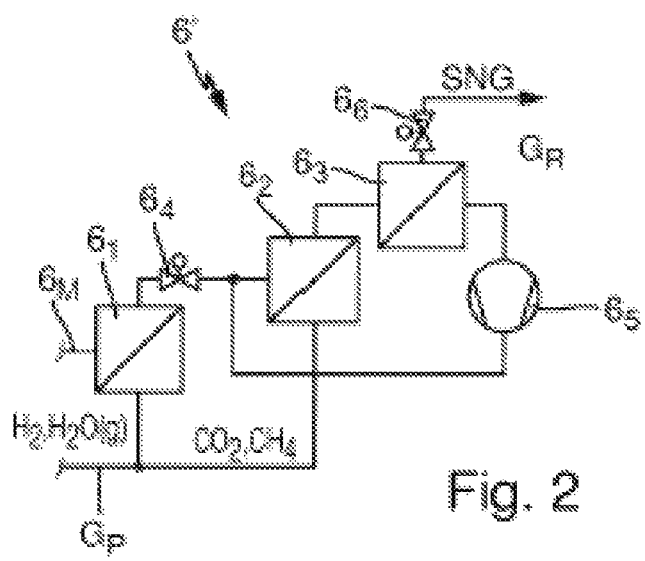
Figure 3:
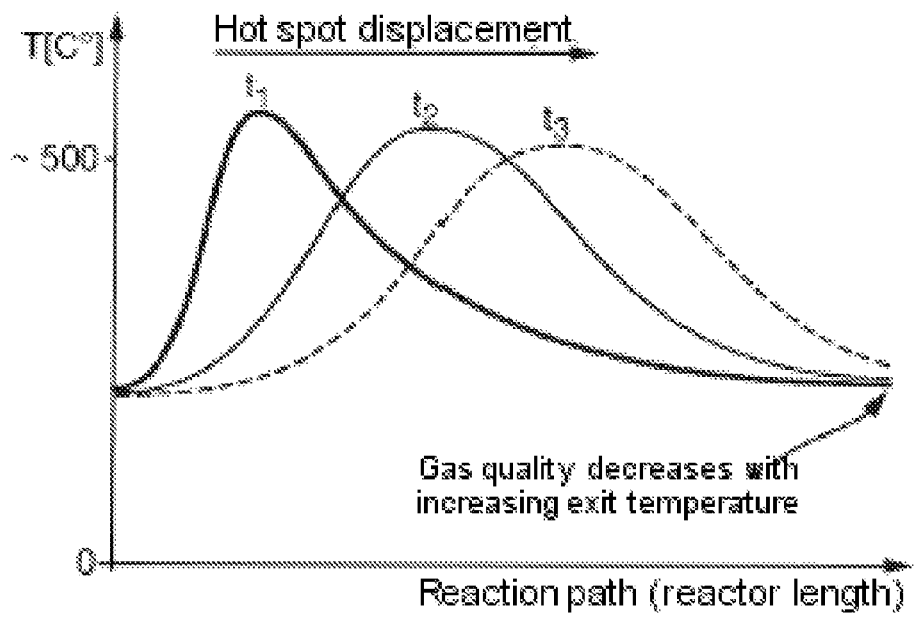
Figure 4:
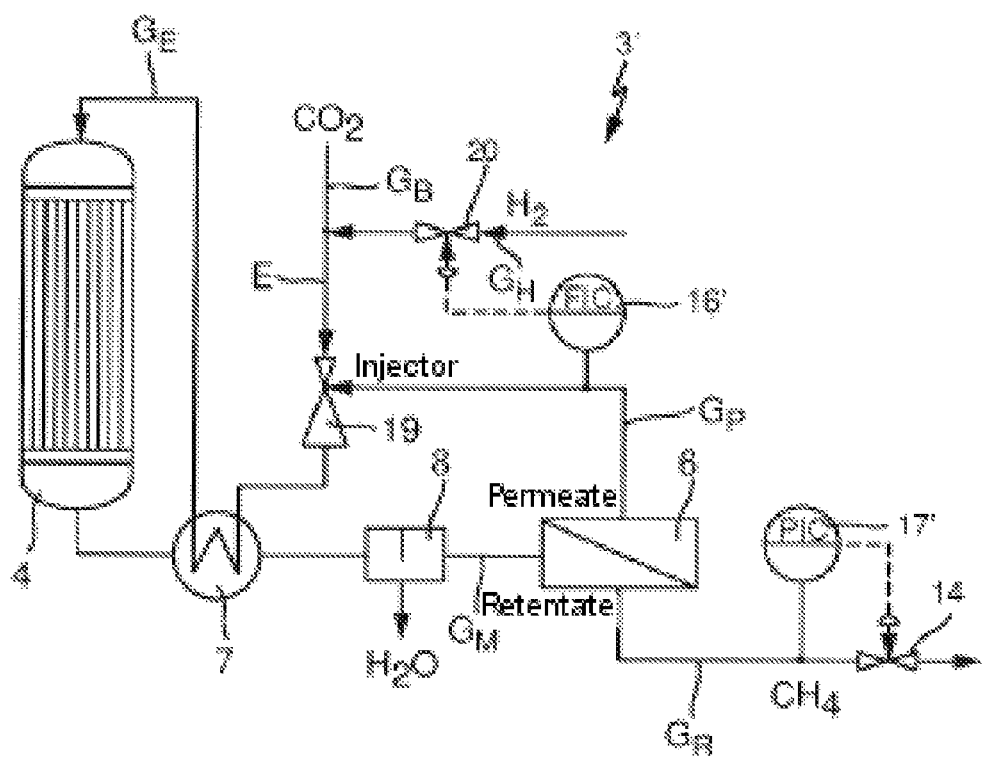

Advantageous embodiments of the invention are depicted in the drawings and are hereinbelow described. In the drawings:

FIG. 1 shows a schematic block diagram of an energy supply system comprising an apparatus for producing a methane-containing substitute natural gas with methanation reactor and downstream gas separation, FIG. 2 shows a block diagram of an exemplary multi-stage realization of the gas separation device of FIG. 1, FIG. 3 shows a characteristic diagram for illustrating a hot spot displacement in the methanation reactor of FIG. 1, and FIG. 4 shows a block diagram of a further exemplary embodiment of an apparatus for producing a methane-containing substitute natural gas.

An energy supply system according to the invention is depicted in FIG. 1 in the form of its components which are of interest herein. The energy supply system comprises a biogas plant 1, which supplies a $CO_2$-rich product gas $G_B$ in a conventional manner, and a hydrogen generating device 2, which supplies hydrogen or a hydrogen-containing gas $G_H$ and which may be, for example, a water electrolysis plant which is operated with renewably generated electric power, for example from wind power and/or photovoltaic plants. These components are connected on their downstream side to the component of primary interest herein, viz., an apparatus 3 for producing a methane-containing substitute natural gas from an input gas E which is formed by metering the hydrogen gas $G_H$ from the hydrogen generating means 2 into the $CO_2$-rich product gas $G_B$ from the biogas plant 1 and thus comprises $CO_2$ and $H_2$ as principal gas components in addition to any minor components such as $CH_4$ and $H_2O$. The device 3 will be more particularly discussed hereinbelow, while regarding the other components of such an energy supply system reference can be made for further details to, for example, the above-cited WO 2010/115983 A1, the content of which is insofar incorporated herein by reference.

The central constituent of the substitute natural gas generating apparatus 3 is a conventionally constructed methanation reactor 4 whereinto the input gas E can be metered via an entry-sided input gas metering means 5. The reactor 4 may be configured as a single stage or be constructed from two or more reactor units arranged in a cascade for example. The methanation reactor 4 is connected on its exit side to a gas separation device 6 which is thus supplied on its entry side with a product gas $G_M$ from the methanation reactor 4. This product gas $G_M$ from the methanation reactor 4 is routed via a heat exchanger 7 and a water separator 8, which may both be bypassed via a bypass line 9, before it enters the gas separation device 6.

According to the invention, the methanation reactor 4 is operated with superstoichiometric hydrogen, as a result of which there is still a noticeable hydrogen fraction present in the product gas $G_M$ of the methanation reactor 4. The gas separation device 6 is designed to remove this unconverted hydrogen together with any unconverted carbon oxide, water and any other minor components, in the form of permeate gas $G_P$, and thereby, with the non-removed gas, supply a methane-containing retentate gas $G_R$ which, depending on quality requirements, is usable as substitute natural gas either directly or via further gas processing.

The gas separation device 6 may be of any of the conventional designs known for this purpose, in particular as a single-stage or multi-stage separation unit of the membrane type. Different membrane types are known for this in the prior art, which may be referenced, depending on the requirements, such as those of the hose membrane type, e.g., pipe modules and capillary/hollow fiber modules, and of the flat membrane type, e.g., plate modules and wound modules.

FIG. 2 shows—as representative of any other usable, conventional gas separation membrane units—a three-stage gas separation membrane unit 6' with three serially, with regard to the retentate gas stream, consecutively connected membrane separation stages $6_1$, $6_2$, $6_3$. A first membrane separation unit $6_1$ separates predominantly hydrogen and water vapor from the supplied product gas $G_M$ of the methanation reactor. The retentate gas from this first stage $6_1$ is supplied via a metering valve $6_4$ to a second membrane separation unit $6_2$, which is specifically designed for the separation of $CO_2$ and $CH_4$. The permeate gas from this middle separation stage $6_2$ is admixed to the permeate gas from the first stage $6_1$ to then form the entire permeate gas stream $G_P$ of this gas membrane separation unit 6'. The retentate gas of the middle stage $6_2$ is supplied to a third stage $6_3$, in which a residual separation takes place, and the permeate gas of this last stage $6_3$ is returned via a compressor $6_5$ to the entry side of the middle separation stage $6_2$. A further metering/pressure valve $6_6$ releases the retentate gas of the third stage as substitute natural gas, i.e., SNG. It will be understood that, as mentioned, any other variants of gas membrane separation devices having one, two or more serial separation stages can be used, in which case, depending on the application scenario, different return loops for permeate gas from a later stage to the entry side of an earlier stage can be provided.

Referring again to FIG. 1, the substitute natural gas generating apparatus 3 includes a permeate gas recycling device 10 whereby the permeate gas $G_P$ is returned from the gas separation device 6 to the entry side of the methanation reactor 4 and is admixed there to the input gas E in order to form an appropriate reactant gas $G_E$ for feeding into the methanation reactor 4. In addition, via a related water feed line 11 water vapor can be metered in for the reactant gas $G_E$. Permeate gas not required for recycling is removed as purge gas $G_{PU}$.

As mentioned, the invention provides that the methanation reactor 4 be operated with super-stoichiometric hydrogen. An open or closed loop control device 12 merely schematically indicated in FIG. 1 is provided for open or closed loop control of the operation of the apparatus 3 such that such a super-stoichiometric hydrogen fraction in reactant gas $G_E$ is permanently maintained for the methanation reaction. This includes not only an open/closed loop control unit as such but also the related peripherals such as sensors and actuators. This is familiar to a person skilled in the art of open/closed loop control and does not require any further elaboration here, so only special features in relation to the substitute natural gas production apparatus 3 will be further discussed here.

The superstoichiometric hydrogen fraction can be characterized by defining a stoichiometry factor S by $$S=([H_2]-[CO_2])/([CO]+[CO_2]).$$

i.e., the stoichiometry factor in this case is defined as the ratio of the difference in the proportions of hydrogen and of carbon dioxide to the sum total of the carbon monoxide and carbon dioxide proportions in the reactant gas $G_E$. On the basis of this definition, a stoichiometric hydrogen fraction in relation to the $CO_2$ quantity corresponds to a stoichiometry factor S=3, the stoichiometry factor S is below three for substoichiometric hydrogen fractions and it is above three for superstoichiometric hydrogen fractions. Preferably, as already mentioned above, the stoichiometry factor is adjusted to values in the superstoichiometric range above three, typically up to a stoichiometry factor of fifteen. As follows directly from the above definition, the stoichiometry factor S and hence the hydrogen fraction in the reactant gas $G_E$ can be changed by varying the added hydrogen quantity and/or the supplied amount of carbon oxides of the input gas E. The amount of hydrogen added is variable in the apparatus 3 not only by means of the hydrogen gas $G_H$ from the hydrogen generating means 2 but also by means of the hydrogen-containing, recycled permeate gas $G_P$.

FIG. 1 explicitly shows some actuators and sensor means which are important in the present case and which are in communication with the open/closed loop control device 12, wherein, in a manner which is conventional and therefore is not more particularly shown therein, the sensor output data are supplied to an input side 12a of the open/closed loop control device 12 and adjustment signals derived therefrom are output by the open/closed loop control device 12 via an output side 12b to assigned actuators.

The actuator means thus comprise in particular the aforementioned input gas metering device 5 and also a permeate gas metering device 13 and a retentate gas outlet valve 14. The sensor means comprise one or more reactant gas sensor elements 15 for measuring the reactant gas volume flow and the reactant gas composition, i.e., the percentage fractions of the various reactant gas components, a permeate gas pressure sensor 16 and one or more retentate gas sensor elements 17 for measuring the pressure, the temperature, the volume flow and/or the composition of the retentate gas $G_R$. Broken lines symbolize which control interventions the open/closed loop control device 12 performs on which actuators on the basis of which sensor data, although this is only a simplifying illustration of one specific example and, as will be readily understood by a person skilled in the art, other open/closed loop control measures are realizable.

In addition, a plurality of sensor elements $18_1$, $18_2$, $18_3$ are arranged in the methanation reactor 4 at successive measuring points in the gas flow direction, each capable of capturing the gas pressure and/or the temperature at the measuring point in question. By virtue of this sensor element arrangement $18_1$, $18_2$, $18_3$ the open/closed loop control device 12 is capable of monitoring the methanation reactor 4 for any hot spot displacement and of thereby adjusting the operation of the methanation reaction and gas separation in response to signs of aging of catalyst material used in the methanation reactor 4 and/or of rectifying such signs of catalyst aging as far as possible.

This is explained hereinbelow with reference to FIG. 3. The sensor elements $18_1$, $18_2$, $18_3$ enable the open/closed loop control device 12 to determine a profile for the temperature trajectory in the methanation reactor 4 along the reaction path and/or reactor length. As will be known, this profile shows a temperature trajectory which initially climbs steeply from the entry side to only come back down gradually, from a maximum called hot spot, owing to the exothermic reaction enthalpy of the reactions taking place in the methanation reactor 4. FIG. 3 illustrates such a temperature profile at three different times, a first time $t_1$ with still unaged catalyst material, a time $t_2$ with already somewhat aged catalyst material and a time $t_3$ with already strongly aged/deactivated catalyst material.

As is apparent from FIG. 3, the hot spot is displaced with increasing catalyst aging away from the reactor entry side, and the maximum decreases somewhat. This hot spot displacement is based on the above-elucidated catalyst deactivation mechanisms and is detectable by the open/closed loop control device 12 from the sensor data in question. The open/closed loop control device is then capable of initiating suitable countermeasures to counteract the effects of catalyst deactivation. For instance, to maintain the retentate gas quality in the face of a detected declining catalyst activity it is capable of raising the pressure in the methanation reactor 4 and/or of increasing the pressure difference between the retentate gas $G_R$ and the permeate gas $G_P$ in the gas separation device 6 by appropriately driving the input gas metering valve 5 and/or the permeate gas metering valve 13 and/or the retentate gas pressure control valve 14. This permits longer on-stream times without replacing the catalyst, so catalyst on-stream times of several years are possible without significant reduction in retentate gas quality. Catalyst deactivation due to carbon depositions on the catalyst is detectable, for example, from the associated pressure drop in the methanation reactor 4. As an open/closed loop countermeasure the water vapor fraction in the reactant gas $G_E$ can be increased, for example by enhanced feeding via the water supply line 11.

FIG. 4 illustrates an alternative 3' of the apparatus 3 of FIG. 1 for producing a methane-containing substitute natural gas from a carbon oxide-containing input gas, where identical and functionally equivalent elements bear the same reference signs for clarity and hence the above description regarding FIG. 1 can be referenced. In the apparatus 3' of FIG. 4, the hydrogen-rich permeate gas $G_P$ is aspirated via an injector 19 and thereby admixed to the input gas E, which in turn consists of a $CO_2$-rich gas, for example the biogas plant product gas $G_B$, and hydrogen gas metered thereinto. The retentate gas outlet valve 14 is controlled by a pressure controller 17' of the related open/closed loop control device, and the rate of addition of hydrogen gas to the $CO_2$-rich gas is controlled via a metering valve 20 by a gas volume flow/mass flow controller 16' of the open/closed loop control device according to the measured volume flow of aspirated permeate gas.

This system design provides that even in the event of stoichiometric metering of the hydrogen gas via the metering valve 20 into the $CO_2$-rich gas, the hydrogen-rich permeate gas $G_P$ additionally added via the injector 19 ensures that the reactant gas $G_E$ comprises superstoichiometric hydrogen. The system process pressure in this plant can be kept constant via a simple admission pressure control. $H_2$ metering is effected in relation to the instantaneous $CO_2$ metering, which serves as control variable. The metering valve 20 is in effect controlled according to the hydrogen quantity injected via the permeate gas stream $G_P$ such that, overall, the desired superstoichiometric hydrogen fraction in the reactant gas $G_E$ remains established.

The methanation reactor 4 was explained above primarily in a design for practicing a chemical methanation, i.e., as a chemical reactor for catalytically supported conversion of the reactants, in particular $CO_2$ with $H_2$, in a temperature range of preferably between 180° C. and 600° C. Alternatively, the methanation reactor 4 can be configured to practice a biological methanation, namely as a biochemical reactor which converts the reactants, in particular $CO_2$ with $H_2$, by means of bacteria in a temperature range of typically below 70° C. The reactant supplied for both types of reactor can alternatively also be biogas, i.e., $CH_4$ and $CO_2$. Establishing a superstoichiometric hydrogen fraction in the reactant gas is also advantageous for conducting the biological methanation. Carbon dioxide converts virtually quantitatively into methane. From the product gas, consisting of the principal fraction $CH_4$ and the $H_2$ added in excess, the $H_2$ fraction has to be separated off to such an extent that the gas satisfies the criteria for gas grid feeding. This separation duty is simpler to perform than the separation of $CO_2$, as unconverted reactant gas, from the product gas. In the reactant gas, carbon monoxide may be substituted, at least to some extent, for the carbon dioxide in corresponding embodiments of the invention.

As is clear from the working examples described above, the invention provides an advantageous way of producing a methane-containing substitute natural gas from a carbon oxide-containing input gas via a chemical or biological methanation reaction wherefor a super-stoichiometric hydrogen fraction in the reactant gas is established by means of suitable open or closed loop control. This ensures virtually complete conversion of a $CO_2$/CO-rich input gas, and the methanation can be operated in an inherently safe way with regard to catalyst deactivation, i.e., catalyst deactivation effects can be counteracted through suitable adjustment of the hydrogen fraction in the reactant gas to the methanation reaction. In addition, the super-stoichiometrically supplied hydrogen fraction, which can be metered with the recycled permeate gas in particular, performs a cooling effect in the methanation reactor to avoid/ameliorate hot spot phenomena.

The invention claimed is:

1. A method for generating a methane-containing substitute natural gas from a carbon oxide-containing input gas, comprising
   subjecting the input gas to a methanation reaction and dividing a product gas obtained therefrom by gas separation into a methane-containing retentate gas, which yields the substitute natural gas, and a hydrogen-containing permeate gas, and returning at least some of the permeate gas to the input gas and admixing therein to form a corresponding reactant gas for the methanation reaction, wherein a superstoichiometric hydrogen fraction is established in the reactant gas for the methanation reaction at all stages of the methanation reaction, and wherein a stoichiometry factor of the reactant gas, which is defined as the ratio of the difference in the proportions of hydrogen and of carbon dioxide to the sum total of the carbon monoxide and carbon dioxide proportions, is maintained above three.

2. The method as claimed in claim 1, wherein a stoichiometry factor of the reactant gas, which is defined as the ratio of the difference in the proportions of hydrogen and of carbon dioxide to the sum total of the carbon monoxide and carbon dioxide proportions, is maintained in the range above three and not more than fifteen.

3. The method as claimed in claim 1, wherein one or more of parameters are measured and used to adjust at least one of an amount of supplied input gas and an amount of returned permeate gas and a hydrogen fraction of the supplied input gas and a pressure in a methanation reactor hosting the methanation reaction and a gas separation pressure difference, wherein the one or more parameters are selected from the group consisting of volume flow of reactant gas, composition of reactant gas, pressure of reactant gas, volume flow of input gas, composition of input gas, pressure of input gas, volume flow of retentate gas, composition of retentate gas, pressure of retentate gas, volume flow of permeate gas, composition of permeate gas, pressure of permeate gas, temperature of reactant gas, temperature of input gas, temperature of retentate gas, temperature of permeate gas, pressure and temperature in the methanation reactor at one or more pressure and temperature, respectively.

4. The method as claimed in claim 3, wherein the permeate gas admixture to the input gas is closed-loop controlled to achieving a specified $CO_2/CO$ minimum conversion according to a specified $CO_2/CO$ gas volume flow of the input gas and a specified pressure difference between retentate gas and permeate gas.

5. The method as claimed in claim 3, wherein the input gas used is a mixture of a $CO_2/CO$-rich gas and of an $H_2$ gas which is metered into the $CO_2/CO$-rich gas according to at least one of the amount of the $CO_2/CO$-rich gas, the composition of the $CO_2/CO$-rich gas, the amount of the returned permeate gas admixed to the input gas and the composition of the returned permeate gas admixed to the input gas.

6. The method as claimed in claim 3, wherein the methanation reactor is monitored for at least one of a catalyst deactivation and a hot spot shift, and once catalyst deactivation/hot spot displacement has been detected, at least one of the following actions are taken: increasing the gas pressure in the methanation reactor, increasing a water vapor fraction in the reactant gas, and adjusting the reactor temperature.

* * * * *